United States Patent [19]

Schlaefer et al.

[11] 4,078,004

[45] Mar. 7, 1978

[54] METHACROLEIN PRODUCTION UTILIZING NOVEL CATALYST

[75] Inventors: Francis W. Schlaefer, Pennsauken, N.J.; George A. Hansen, Philadelphia, Pa.

[73] Assignee: Rohm and Haas Company, Philadelphia, Pa.

[21] Appl. No.: 428,150

[22] Filed: Dec. 26, 1973

Related U.S. Application Data

[60] Division of Ser. No. 178,434, Sep. 7, 1971, Pat. No. 3,839,227, and a continuation-in-part of Ser. No. 149,343, Jun. 2, 1971, abandoned.

[51] Int. Cl.² .............................................. C07C 45/04
[52] U.S. Cl. ................................................. 260/604 R
[58] Field of Search ..................................... 260/604 R

[56] References Cited

U.S. PATENT DOCUMENTS

| | | | |
|---|---|---|---|
| 2,974,161 | 3/1961 | Keith et al. | 260/604 R |
| 3,098,102 | 7/1963 | Bethell et al. | 260/604 R |
| 3,308,070 | 3/1967 | Miller | 252/455 |

OTHER PUBLICATIONS

Takamasa et al., Chem. Abst., Vol. 71, item 129218x, 1969.

*Primary Examiner*—James O. Thomas, Jr.
*Assistant Examiner*—Werren B. Lone

[57] ABSTRACT

The present invention relates to the discovery of a new catalyst support and in methods for the preparation of olefinic oxidation products such as unsaturated acids, nitriles, and aldehydes. The novel support for the oxidation catalysts is expanded, crushed perlite, that is, volcanic glass which has been expanded to tiny hollow bubbles by heat which are then fractured. Perlite is a siliceous material largely of $SiO_2$. Surprisingly, it is greatly superior to the commonly used amorphous, colloidal silica as a support, as well as to other known supports. The result is high productivity of desired products over a prolonged period of operation, high selectivity over a prolonged period of operation and prolonged life of the oxidation catalyst systems. The invention is preferably employed in the preparation of unsaturated aliphatic acids such as methacrylic acids and unsaturated aldehydes such as methacrolein by the oxidation of the appropriate aldehyde or olefin.

13 Claims, No Drawings

METHACROLEIN PRODUCTION UTILIZING NOVEL CATALYST

This is a division of application Ser. No. 178,434 filed Sept. 7, 1971 now U.S. Pat. No. 3,839,227, and a continuation-in-part of Ser. No. 149,343 filed June 2, 1971 now abandoned.

The invention relates to the preparation of unsaturated carboxylic acids and unsaturated aldehydes, or unsaturated nitriles, by the oxidation of the corresponding aldehyde or olefin. Methacrolein, in particular, is prepared by the oxidation of isobutylene. Methacrylic acid is also obtained in a minor proportion.

Many attempts and many catalyst systems have been employed by the art to achieve conversion of propylene to acrolein, acrylic acid and acetic acid and of isobutylene to methacrolein and methacrylic acid. The art indicates that the conversion requires high temperatures and large volumes of gases. These conditions foster substantial costs in the construction and maintenance of reactors. Accordingly, for maximum commercial utility, it is imperative that productivity be maintained at a high level. Various degrees of success have been achieved by prior art systems by resorting to the use of high oxygen-propylene ratios, high reactor temperatures and various combinations of promoters and catalysts. The high ratios and temperatures favorably affect productivity per reactor volume but lead to increased waste gas formation. Also, promoters tend to be volatile and toxic, thereby requiring additional equipment for control and reuse. By and large, the known processes present the possibility and actual realization of increased waste gas formation, toxicity problems from the use of volatile promoters, expensive reactor construction and inefficient operation due to catalyst deterioration.

The patent literature abounds with statements to the effect that a given catalyst is useful for the preparation of aldehydes from unsaturated olefins, and implications are sometimes made that a given catalyst is equally efficacious for oxidizing propylene and for oxidizing isobutylene to give, respectively, acrolein and methacrolein. The applicants have found this is not the general rule. A catalyst support which provides activity of a nature to convert propylene to acrolein, when utilized with isobutylene, results in excessive conversion of starting material to waste products such as carbon monoxide and carbon dioxide. Conversely, a catalyst useful for converting isobutylene to methacrolein results in a very low conversion of propylene to desired products. For example, when pyrogenic colloidal silica is utilized as a support for a catalyst containing cobalt molybdate or iron molybdate, it is excellent for converting propylene to acrolein, but results in excessive waste products when utilized with isobutylene at useful reaction temperatures.

It has now been found that expanded, crushed perlite provides a superior support for catalysts containing cobalt molybdate, iron molybdate, and other oxidation catalysts, and particularly when the perlite-supported catalyst is utilized in the vapor phase oxidation of isobutylene to methacrolein.

In addition to the preferred cobalt-molybdate and iron-molybdate based catalysts exemplified below, others are useful. These include the substitution for, or addition to molybdenum, of tungsten. Many other known metal oxide based vapor phase oxidation catalysts, when used with the perlite support as taught by applicants, are of benefit.

The objects and advantages of the highly critical nature of the support and resulting catalysts are as follows:

(1) High productivity over a prolonged period

The examples following this section demonstrate that the methacrolein-methacrylic acid productivity using the conditions of the present invention is substantially higher than that obtained with other conditions. Furthermore, this high productivity is maintained even after extended periods of operation. This stability of production is particularly important in commercial operations where decreases in the aldehydes and/or acid content of the stream substantially reduce the efficiency of the equipment used to isolate the aldehydes and/or acids.

(2) High selectivity over a prolonged period

By employing the catalysts of the present invention, one can increase the methacrolein-methacrylic acid productivity without being burdened by an increased rate of overoxidation. This not only results in efficient use of the isobutylene, but also reduces the substantial heat load caused by the production of waste gas and acetic acid. This results in more efficient reactor utilization and also produces a higher concentration of desired aldehydes and/or acids in the reactor effluent. This enables the subsequent isolation of the aldehydes and/or acids to proceed with maximum efficiency.

(3) Prolonged physical stability and activity

In the field of catalysis, physical stability normally refers to the ability of a catalyst to withstand pressure and abrasion. Such are encountered in heterogeneous catalytic reactors and cause less stable catalysts to crumble into smaller particles or fines. The occurrence of the latter is particularly undesirable in that they restrict gas flow through the reactor. Ultimately, a point is reached where the pressure drop is appreciable and flow becomes nearly impossible. The catalyst must then be replaced. Loss of activity also requires catalyst replacement. Since commercial reactors normally contain a plurality of small diameter tubes, frequently several thousand or more, catalyst replacement is exceedingly time consuming. In addition to the lack of productivity during shutdown, one must also bear the economic burden of synthesizing and charging fresh catalyst more frequently.

The present invention comprises a process whereby oxygen and isobutylene are continuously reacted to produce the corresponding aldehyde and acid. The invention is particularly concerned with the use of perlite as an unexpectedly superior catalyst support.

Perlite ore is a natural volcanic glass containing 2 to 6 percent of bound or entrapped water, that is, water which is retained after drying overnight in an oven at 105° C. It normally contains 70 to 75 percent silicon dioxide, 10 to 15 percent alumina, 5 to 10 percent of a total potassium oxide and sodium oxide, and small amounts of the oxides of phosphorus, manganese, calcium, iron, magnesium, sulfur, and titanium.

Perlite, intumesced or expanded and not expanded, has been used for many purposes. For example, the expanded perlite has been used for purposes where its extremely low bulk density is of value as in building plaster aggregate, as a filter aid, or in concrete aggregates, as a loose-fill insulation in buildings, and in other applications, as a soil conditioner, as a filler or pigment, and so on. The ore itself has been used as a catalyst support, for example, when coated with copper chloride and used as relatively large particles having certain fractions between 0.145 and 0.246 millimeters and another fraction between 0.99 and 1.99 millimeters (63 Chem. Abstracts 13056 and 13057). The catalyst was used in the oxidative chlorination of propylene.

The ore is produced in the western and southwestern states and is shipped to other places including eastern states where it is expanded and utilized, for example, as insulation. The ore must be vitreous; devitrified ore does not expand satisfactorily.

By "expansion" of perlite is meant the phenomenon that occurs when the ore is quickly heated to high temperatures, for example, by a flame, the result being a frothy light-colored intumesced mass of glassy bubbles or microballoons. Utilizing the proper particle size of raw ore, it is possible to get bubbles of the order of 1 mil to 5 mils in diameter, having walls of the order of a fraction of a micron to several microns in thickness. These bubbles are formed by the moisture within the particles of perlite, in the form of steam, which quickly expands when the temperature of the perlite particles becomes such that the glass is soft enough to be plastically deformed by the expanding steam. Normally the temperature at which the perlite particles become expanded is in the range of about 760° to 1093° C. The particles are carried by the combustion gases of the flame in fluidized form to collection devices such as cyclones, and during the agitation and physical contact of the particles and the equipment, the bubbles are commonly fragmented to form smaller curled chips which are of such a configuration that they confer a very low bulk density upon the collected product. Hereinafter, whenever the word "perlite" is used, expanded perlite is meant, the more or less whole bubbles or spheres being equally as useful as the chips which may, of course, be formed during handling and use.

The perlite used according to the invention has certain critical characteristics as regards surface area, pore size, pore size distribution, and total porosity. For example, a silica catalyst support suitable for converting propylene to acrolein desirably has a surface area in the neighborhood of 40 to 50 m.$^2$/g., is unsuitable for converting isobutylene to methacrolein. The perlite useful in accordance with the invention has the following properties:

| Properties | Useful Range | Preferred | Most Preferred |
|---|---|---|---|
| total surface area, m.$^2$/g. | <15 | <10 | <5 |
| total porosity, cc./g. | >2.5 | >2.8 | >3 |
| pore size distribution | | | |
| >100,000 A (macropores) | <40% | <55% | <60% |
| 100,000 A to 10,000 A (medium size pores) | the balance | | |
| 10,000 A to 1,000 A (micropores) | <15% | <10% | <6% |
| <1,000 A (micropores) | <10% | <5% | <4% |

The pore size distribution is expressed as a percentage of the total pore volume. Another desirable feature is the particle size of the perlite. It should pass through a 325 mesh screen, U.S. Sieve Series. Preferably, 75 to 100 percent passes through a 400 mesh screen. Silica has quite a different pore size distribution, having much fewer macropores (>100,000 A), about the same medium range (the "balance" in table above), and much more in the microporous range of pore size (<10,000 A).

Various prior art supports for catalysts for oxidizing propylene to acrolein or purportedly isobutylene to methacrolein include silica, diatomaceous earth, kieselguhr, silicon carbide, clay, aluminum oxides, carbon, pumice, alundum, titania, Carborundun, colloidal, silica, porcelain, bentonite, bauxite, silica gel, glass, fused quartz, coke, metallic aluminum, iron, copper, nickel, cobalt, or chromium, vermiculite, pyrogenic oxides of colloidal fineness prepared by oxidation of the halides of aluminum, zirconium, titanium, and silicon in the presence of steam at temperatures of about 1000° F., pozzoluana, dawsonite, montmorillonite, green sand, zeolites, permutites, activated carbon, crushed brick, magnesia, asbestos, mineral wool. None are known to be as good as perlite, especially for long term usefulness in the vapor phase oxidation of isobutylene to methacrolein.

The perlite is used as a support rather than a diluent, i.e., the catalyst is formed in the presence of the perlite suspended in liquid, and then the mixture is dried so that the catalyst appears on the surface of the perlite flakes and is not simply intermingled physically therewith.

Substantially any catalyst having some activity for the conversion of propylene and/or isobutylene to the corresponding aldehyde is useful for providing much improved selectivity in the yield of methacrolein from isobutylene when utilizing the perlite support of the invention. In other words, the most critical consideration in the oxidation of isobutylene to methacrolein is the support—not the catalyst, although the latter is also important. One useful class of catalysts is represented by the following: $Sb_{0.0001-.1}Sn_{0.0001-.1}$ $Te_{0.001-1}As_{0-.1}A_{0-.1}/Mo_{12}Fe_{2-12}Sb_{0.05-1}Th_{0.01-1}U_{0-.2}Si_{0-50}P_{0.001-.5}Ox$, wherein A is Bi and/or Cd. The slash mark (/) dividing the left-hand portion and right-hand portion indicates that the materials on the left portion are added as promoters and in the form of water-insoluble compounds such as the tellurides. The materials on the right-hand portion are added as water-soluble compounds, it being understood that the materials are present in the final catalyst as the oxides resulting from calcining at a high temperature in the presence of air. The symbol "Ox" indicates that oxygen is combined with the elements to the extent necessary and inherent in the calcination process.

Another suitable catalyst is $Sb_{0-0.1}Sn_{0-0.1}Te_{0.001-1}As_{0-.1}A_{0-.1}/Mo_{12}Co_{2-12}Sb_{0-.1}Th_{0.01-1}U_{0-.2}Si_{0-50}P_{0-.5}Ox$. Still others are represented by the following, which make apparent that although a catalyst based on oxides of cobalt or iron with molybdenum (sometimes referred to as cobalt or iron molybdates) are preferred, many other catalysts based on oxide combinations, usually with promoters or activators, are useful.

$Co_7Mo_{12}Sn_1Te_2Ox$,
$Co_{1-16}Sn_{1-3}Mo_{6-24}Te_{0.2-4}Ox$,
$W_{0.5-6}Co_{1-16}Sn_{1-3}Mo_{6-24}Te_{0.2-4}Ox$,
$Co_{1-15}Sn_{1-3}Mo_{6-24}Te_{0.2-4}Ox$,
$Fe_{0.1-12}Bi_{0.1-12}P_{0-10}Mo_{12}Ox$,
$Co_3Mo_{12}Ox$,
$Bi_{0.1-12}P_{0-10}Mo_{12}Ox$,
$Fe_3Mo_{12}Ox$,
$Bi_{0.1-12}Fe_{0.1-12}P_{0.1-2}B_{0.1-4}Mo_{12}Ox$,
$Mo_{12}Fe_{4.5}Bi_{4.5}As_2Ox$,
$Fe_{0.01-10}Co_{0.5-2}Mo_{0.5-2}Te_{0.01-.1}Ox$,
$Mo_{10}Te_{1-10}M_{2-20}P_{2-20}Ox$, e.g.,
$Mo_{100}Te_{33.33}Mg_{66.6}P_{66.6}Ox$
(M = group II - A metal, Ca, Sr, etc.),
$Mo_{10}Te_{1-10}M_{2-20}P_{2-20}Ox$
(M = Zn or Cd), $Cu_9Te_9PMo_{12}Ox$,
$Sb_{1-99}Fe_{1-50}Ox$
promoted with 0.01 to 20 percent by weight of the total of Bi, Sn, Nb, Te, W, Cd, Zr, Co, Mo, Zn, Ba, Ca, or As,
100 $MoO_3$; 10-100 $TeO_2$; 10-100 $ThP_2O_7$ (molar basis),
$Cu_{8-10}Te_{1.3-1.7}P_{1-1.2}Mo_{12}Ox$,
$Bi_{0.5-18}P_{0-5}Mo_{12}Ox$,
$Mo_{10}Te_{1-10}Mn_{2-20}P_{2-20}Ox$,
$Bi_{4-36}P_{0-2}Mo_{12}Ox$,
$Bi_{4\ or\ more}P_{0-2}Mo_{12}Si_{24-160}Na_{0-3}Ox$,
$Sb_1M_{50}$ to $Sb_{99}M_1Ox$
where M = U, Fe, Mn, Th, Ce, Mo, or Sn,
$Sb_{1-99}Mn_{1-50}Ox$,
$Ni_{0-20}Co_{0-15}Fe_{0.7-7}Bi_{0.1-4}P_{0.1-2}Mo_{12}Ox$ wherein amount of Ni + Co = 2-20
$P_{0-3}Te_{3-15}Mo_{5-20}Ox$ with 20-50 moles $Al_2O_2$,
$Bi_{.1-12}Fe_{.1-12}P_{.1-2}B_{.1-4}Mo_{12}Ox$,
$Co_{1-16}Sn_{1.5}Mo_{12}Te_{0.1-6}Ox$.

The foregoing catalyst compositions may be prepared by the methods taught in the following U.S. patents:

| | |
|---|---|
| 3,065,264 | 3,439,045 |
| 3,164,628 | 3,445,521 |
| 3,200,081 | 3,446,840 |
| 3,248,340 | 3,464,931 |
| 3,341,471 | 3,467,716 |
| 3,392,196 | 3,475,488 |
| 3,408,309 | 3,520,923 |
| 3,415,886 | 3,542,843 |
| 3,423,329 | 3,546,138 |
| 3,423,331 | |

Note also British Pat. No. 1,128,031. The preparation of these catalysts, except for the combination thereof while admixed with perlite, form no part of the present invention. These patents are incorporated by reference to the extent necessary to enable those skilled in the art to prepare the catalysts.

As may be seen, the catalysts are essentially based on oxides of the following combinations, with added modifiers and activators.

| | |
|---|---|
| Co-Mo | Sb-U, Fe, Mn, Th, Ce, Mo, or Sn |
| Fe-Mo | Mo-Zn or Cd |
| Co-W | Mo-Th |
| Fe-W | Mo-P |
| Te-Mo | Cu-Te |
| Bi-Mo | Mo-Ca or Mg |
| Bi-Fe | |

Another cobalt-molybdate-containing catalyst is the one shown in our application Ser. No. 615,880, now U.S. Pat. No. 3,527,716, or in our application Ser. No. 783,641. As described in said patent, one may incorporate, by fluxing, the calcined cobalt molybdate with one or more of the tellurides of arsenic, bismuth and antimony, which may be represented by the formulas: $As_2Te_3$, $Bi_2Te_3$ and $Sb_2Te_3$, respectively. Usually, one would employ one of these tellurides in any particular catalyst system but it is quite possible to react mixtures of two or all three of these tellurides with the cobalt molybdate, as described hereinafter. The tellurides are employed in such a particle size that 75 percent is in the mesh range of 80 or greater. It is desirable to employ at least 90 percent of the telluride in the mesh range of 80 or greater and most advantageous to have all of the telluride in the mesh range of 80 or greater. The preferred telluride is that of bismuth. Fluxing is conducted at a temperature of between 420° and 600° C. This catalyst system may be used, as described hereinbefore, either promoted or not. If a promoted catalyst system is contemplated, it is preferred to use copper telluride, $Cu_2Te$, as the promoter.

The catalyst system is employed in the oxidative preparation of methacrolein and methacrylic acid by the reaction of isobutylene, oxygen and water. A temperature range of about 350° to about 500° C., preferably from 350° to about 460° C. is used. Atmospheric pressure or pressures somewhat above atmospheric, such as about 1 to about 40 atmospheres, may be used. Usually atmospheric pressure is employed.

Oxygen may be used as such in the reaction or may be supplied as air. It is desirable in this reaction to employ a diluent to facilitate control of this highly exothermic reaction. Therefore, if oxygen is employed as such, it is preferred to employ a gaseous diluent, such as carbon dioxide, nitrogen or the like. The carbon dioxide diluent is most economically provided from the carbon dioxide produced in the process. If oxygen is employed as the normal approximately 20 percent component of air, then nitrogen is already present as a useful diluent. Generally, the use of oxygen as a component of air is quite satisfactory for the purposes of this reaction.

The isobutylene is employed in a ratio with respect to oxygen of 1:0.2 to 1:3, preferably 1:0.8 to 1:1.2.

The ratio of water to isobutylene is about 1:1 to 10:1, preferably about 2:1 to 6:1. The contact time can range from 20 seconds to as low as 0.1 second, but about 0.5 to about 5 seconds is preferred. Longer contact times generally produce higher conversions, but this is accompanied by an increase in waste gas formation. One skilled in the art may balance these two factors to obtain the contact time which results in the most economical operations.

The oxygen level in the feed is such as to result in an effluent from the reactor which contains at least 1.5 percent of oxygen. The upper level of oxygen, as a practical matter, is such that about 20 percent of oxygen is used in the feed. As to isobutylene in the feed, it ranges from about 5 percent to an absolute maximum of 20 percent. Water vapor in the feed is an absolute minimum of 15 percent and may range up to about 60 percent.

To assist those skilled in the art to practice the present invention, the following modes of operation are suggested by way of illustration, ratios and percentages being by weight and the temperatures in ° C. unless otherwise specifically noted. Exceptions are the catalyst, which is expressed in terms of atomic or mole ratios, and the vaporized reactants which are in volume percents (the same values also indicating mole percents).

An aqueous solution, prepared by dissolving 592 grams of cobaltous nitrate hexahydrate in 700 ml. of deionized water, previously warmed to 60° C., is added to another solution which is prepared from 354 grams of ammonium heptamolybdate and 500 ml. of deionized water, previously warmed to 75° C. and containing 120 grams of perlite. The resulting solution is agitated and maintained at 48° to 50° C., while 320 ml. of aqueous 15 percent ammonia is added, dropwise, over a 30 minute period. After agitating for another 15 minutes, the slurry is suction filtered and the precipitate washed on the funnel with five one-liter portions of deionized water. The filter cake is then allowed to stand under one liter of deionized water for 72 hours. After removing the remaining water by filtration, the filter cake is reslurried with one liter of deionized water for one hour and filtered again. This filter cake is calcined at 520° C. in the presence of a 6 liter per minute air stream.

The supported cobalt molybdate so obtained is crushed to 10/20 mesh. A paste of the supported cobalt molybdate and bismuth telluride in a weight ratio of cobalt molybdate to bismuth telluride of 300:1.67 is formed, shaped into pellets, dried, and fluxed at a temperature of 470° to 490° C.

EXAMPLE 1

A catalyst conforming to the formula $Sn_{0.051}Sb_{0.051}Te_{0.535}/Fe_{9.7}Mo_{12.0}P_{3.57}Sb_{0.204}Th_{0.051}Ox$ is prepared as follows:

A 2 l. resin flask is charged with 90.8 g. phosphomolybdic acid ($20MoO_3 \cdot 2H_3PO_4 \cdot 48H_2O$), 154 g. ferric nitrate ($Fe(NO_3)_3 \cdot 9H_2O$), 10.4 g. 87 percent phosphoric acid, 1.0 g. thorium nitrate ($Th(NO_3)_4 \cdot 4H_2O$), 40 ml. 71 percent nitric acid, 890 ml. deionized water and 95 g. perlite having a surface area of <5 m.$^2$/g., a total porosity of about 2.8 cc./g. over 60 percent macropores, and less than about 7 percent micropores, 100 percent of which passes a 325 mesh sieve. The contents are then stirred at 60° to 65° while 342 g. of a 15 percent ammonia solution is added dropwise over a period of 35 minutes. Agitation of the thick slurry is continued while 2.5 g. antimony telluride ($Sb_2Te_3$), 1.5 g. molybdenum ditelluride ($MoTe_2$), 0.5 g. tin antimonide (SnSb) and 26 g. of the same perlite is added. The temperature is then raised and, while agitating, water is stripped off until a thick paste is obtained. The latter is formed into 3/16 inch × 3/16 inch pellets and calcined in an air stream for 8 hours at 400° C. A 1 inch × 32 inches tubular reactor, equipped with a preheater is charged with a mixture of 55.2 g. of the above and 113 ml. of nickel helices and then heated in a molten salt bath at 406° C. A feedstream containing 4.7 percent isobutylene, 13 percent oxygen, and 36 percent steam, nitrogen forming the balance. A high yield of methacrolein is obtained. Small amounts of methacrylic acid, acetone, acetaldehyde, formaldehyde, 2,3-butanedione, carbon monoxide, and carbon dioxide are also obtained.

When the same catalyst is used for oxidizing propylene to acrolein, using a temperature of about 470° C. (this reaction gives better results at higher temperatures than for isobutylene oxidation), only a low yield of acrolein is obtained.

When this catalyst on perlite is calcined at 600° C., similar results are obtained except that it is virtually ineffective for propylene oxidation.

EXAMPLE 2

A catalyst prepared similarly with a perlite support but having the formula $Sn_{0.0376}Sb_{0.0376}Te_{0.451}/Fe_{7.13}Mo_{12.0}P_{3.59}Sb_{0.15}Th_{0.0376}Ox$ gives similar results.

EXAMPLE 3

A catalyst conforming to the formula $Bi_{0.0578}Sn_{0.136}Sb_{0.136}Te_{1.64}/Fe_{7.1}Mo_{12.0}Si_{20.4}P_{2.54}Sb_{0.136}Th_{0.0327}Ox$ is prepared as follows:

A 2 l. resin flask equipped with a stirrer is charged with 95 g. colloidal silica, 181.6 g. phosphomolybdic acid, 21 g. 87 percent phosphoric acid, 308 g. ferric nitrate, 2.0 g. thorium nitrate, 694 ml. water and 56 ml. 71 percent nitric acid. The mixture is stirred at 60° to 65° while 509 g. of 14 percent aqueous ammonia solution is added over 40 minutes. Stirring is continued while 5.0 g. antimony telluride, 3.0 g. molybdenum ditelluride, 1.0 g. tin antimonide and 26 g. of colloidal silica are added. The stirred slurry is then converted to a thick paste by boiling off the excess water. The paste is bulk calcined for 8 hours in air at 612° to 635° C. This is ground to 60+ mesh and 115.5 g. charged to a 2 l. resin flask along with 0.77 g. tin antimonide, 7.12 g. molybdenum ditelluride, 0.85 g. bismuth telluride ($Bi_2Te_3$), 4.08 g. colloidal silica and 180 ml. deionized water. The slurry is heated, with stirring, to produce a loose paste. The latter is then used to coat 151 g. of silicon carbide which was previously impregnated with 5 w/w percent molybdenum trioxide. The granules are dried and then calcined for 8 hours at 426° to 442°. The yield of acrolein from propylene using conventional vapor phase oxidation conditions was about 37 percent, whereas isobutylene similarly oxidized gave a yield of only 25 percent methacrolein, with only 38 percent conversion of isobutylene to products. This shows that nonperlite supports are less effective in isobutylene oxidation.

EXAMPLE 4

Similar results to Example 3 are obtained using similarly prepared catalysts of the formulas $Sn_{0.051}Sb_{0.051}Te_{0.612}/Fe_{4.85}Mo_{12.0}Si_{0.56}P_{3.57}Sb_{0.204}Th_{0.051}Ox$ and $Sn_{0.0522}Sb_{0.0652}Te_{0.807}/Fe_{8.6}Mo_{12.0}Si_{8.52}P_{1.05}Th_{0.0391}Sb_{0.195}Ox$ supported, respectively, on colloidal silica and on Allundum. The first is a moderately good catalyst for oxidizing isobutylene to methacrol in but ineffective for propylene oxidation, contrary to the usual poor behavior of catalysts on silica supports, when oxidizing isobutylene, for reasons unknown. Perlite as a support far outperforms silica for oxidizing isobutylene. The second catalyst gives moderate yields, of both aldehydes.

EXAMPLE 5

A perlite-supported catalyst of the composition $Sn_{0.05}Sb_{0.08}Te_{0.52}/Fe_{9.85}Mo_{12.0}P_{3.56}Sb_{0.26}Th_{0.05}Ox$ is prepared as follows:

A 2 l. resin flask is charged with 90.8 g. phosphomolybdic acid ($20MoO_3 \cdot 2H_3PO_4 \cdot 48H_2O$), 154 g. ferric nitrate [$Fe(NO_3)_3 \cdot 9H_2O$], 10.4 g. 87 percent phosphoric acid ($H_3PO_4$), 1.0 g. thorium nitrate ($Th(NO_3)_4 \cdot 4H_2O$), 40 ml. 70 percent nitric acid, 888 ml. deionized water and 95 g. perlite. The contents are then stirred at 60° to 65°, while 308 g. of a 15 percent ammonia solution is added dropwise over a period of 40 minutes. Agitation of the thick slurry is continued while 3.1 g. antimony telluride ($Sb_2Te_3$), 1.5 g. molybdenum ditelluride ($MoTe_2$), 0.5 g. tin antimonide (SnSb) and 26 g. perlite are added. The temperature is raised and, while agitating, the water is stripped off until a thick paste is obtained. The latter is formed into 3/16 inch × 3/16 inch pellets, dried and calcined in an air stream for 8 hours at 511° C.

A 1 inch × 32 inches tubular reactor, equipped with a preheater is charged with a mixture of 55.2 g. of the above and 113 ml. of nickel helices and then heated in a molten salt bath at 360° C. while a feedstream containing 4.7 percent isobutylene, 13.1 percent oxygen, 36.4 percent water and the balance nitrogen is passed over the bed. This results in a reactor temperature of 372° C. Product distribution data are shown in Table I. Subsequent to this test the bath is raised to 398° C. and another run made at a reactor temperature of 425°. Feeds are similar to those used in the preceding test. Data are shown in Table I.

EXAMPLE 6

A silica-supported catalyst of the following composition $Sn_{0.05}Sb_{0.07}Te_{0.52}/Fe_{9.85}Mo_{12.0}P_{3.56}Sb_{0.19}Th_{0.05}Ox/SiO_2$ is prepared.

Synthesis of this composition is generally similar to that used in Example 5. However, the calcining temperature is raised to 625° C. in an attempt to reduce the surface area in order to minimize the over-oxidations (relative to perlite) encountered when this type of support is used in oxidation of the sensitive $C_4$ hydrocarbons. The oxidation test is conducted at a reactor temperature of 370° C. and the data are shown in Table I. The silica is an amorphous colloidal pyrogenic silica commonly used for a support for vapor phase oxidation catalysts.

The data in Table I clearly indicate the superiority of the perlite support. Thus, at the 372° test, the perlite support results in much higher conversions to the desired product, methacrolein. This, moreover, is accomplished at the expense of over-oxidation to waste gas.

The finished catalyst material with a perlite support has about 90 percent of its pores of greater than 10,000 A in size, the bulk falling in the range of 10,000 A to 100,000 A. The silica supported catalyst has about 90 percent of its pores in sizes below 10,000 A, the bulk being in the 1,000 A to 10,000 A range. The original perlite support as such has a surface area of 1.8 m.$^2$/g., about 65 percent of the pores being greater than 100,000 A in size, about 30 percent between 10,000 A and 100,000 A, and only about 5 percent below 10,000 A.

Table I
Comparison of Perlite with Silica, A Support Preferred by Prior Art

| Example | Reactor Temp. (°C.) | Conv. of $C_4H_8$(%)[4] | Percent Conversion to[3] | | | |
|---|---|---|---|---|---|---|
| | | | MAcr[2] | MAA | HAc | Waste Gas |
| 5 (perlite support) | 372 | 44 | 29.9 | 0.6 | 1.7 | 5.5 |
| | 425 | 97 | 72.5 | 1.5 | 1.6 | 17.4 |
| 6 (SiO$_2$ support) | 370 | 33 | 10.7 | 0.3 | 0.9 | 14.3 |
| | 425[2] | | | | | |

[1]By difference.
[2]Runaway exotherm did not permit steady state operation.
[3]MAcr = methacrolein
MAA = methacrylic acid
HAc = acetic acid
[4]$C_4H_8$ = isobutylene

EXAMPLE 7

A catalyst of the formula $Sn_{0.05}Sb_{0.07}Te_{0.75}As_{0.12}/Fe_{8.35}Mo_{12.0}P_{3.03}Sb_{0.19}Th_{0.05}Ox$ is prepared as follows:

Perlite (95 g.) is slurried with 90.8 g. phosphomolybdic acid, 154 g. ferric nitrate, 1.0 g. thorium nitrate, 10.4 g. 85 percent phosphoric acid, 60 ml. 70 percent nitric acid and 810 ml. deionized water. The slurry is agitated at 50° to 63° C. while 390 g. of a 14 percent ammonia solution was added, dropwise, over a 45 minute period. Agitation is continued while a mixture of promoters comprising 2.0 g. molybdenum telluride, 3.1 g. antimony telluride, 0.5 g. tin antimonide, 1.4 g. arsenic telluride, 26.0 g. perlite and 12.6 g. molybdenum trioxide is added. The slurry is agitated vigorously while enough water is stripped to yield a paste amenable to pelletization. After pelletization, the 3/16 inch × 3/16 inch segments are dried, tumbled with 0.2 g. 200+ mesh arsenic telluride and then calcined in air, at 481° for 8 hours.

The catalyst is tested for acrolein production in a manner similar to that outlined above, with propylene being substituted for the isobutylene feedstock. Here, using a reactor temperature of 468°, 49 percent of the propylene is consumed with 32 percent of that fed going to acrolein and 4.7 percent to acrylic acid. Respective conversions to acetic acid, acetaldehyde, formaldehyde and waste gas are 0.1, 0.0, 1.8, and 10.2 percent. This suggests the perlite-supported catalyst is useful primarily for isobutylene oxidation.

EXAMPLE 8

The catalyst $Bi_{0.15}Te_{0.65}/Co_{10.6}Mo_{12.0}U_{1.30}Ox$ is prepared as follows:

A solution containing 110 g. ammonium heptamolybdate, 182 g. cobaltous nitrate hexahydrate and 375 ml. deionized water is heated to 51° and slowly added to a stirred slurry of 36.6 g. perlite and 148 ml. deionized water at 49° C. Agitation at 52° to 55° is continued while 98 g. of 15 percent ammonia is added over a 15 minute period. Subsequent to this, 6.6 g. molybdenum telluride, 8.9 g. molybdenum trioxide, 4.0 g. bismuth trioxide, 20.8 g. uranium trioxide and 36.6 g. perlite are added to the well agitated slurry. The latter is then heated to drive off most of the water, extruded, dried and calcined in air for 8 hours at 399°. In the standard methacrolein production test outlined above, 72 percent of the isobutylene is converted at a reactor temperature of 400°, with 37.4 percent of that fed going to methacrolein. Conversions to methacrylic acid, acetic acid, acetaldehyde, formaldehyde and waste gas are 1.8, 3.7, 0.7, 1.5 and 25.2 percent, respectively.

This shows that a cobalt molybdate based catalyst is also useful.

EXAMPLE 9

The catalyst is identical to that of Example 8 but the feedstream contains 3.2 percent acrolein and a trace (0.3 percent) of propylene in addition to 6.3 percent oxygen, 50.0 percent nitrogen and 40.0 percent steam. The total gas feed is 1.5 l./min. while the catalyst charge is 100 g. Using a reactor temperature of 370°, 27 percent of the acrolein and 53 percent of the propylene feed are consumed. Based on the total $C_3$ reactants fed, 11.0 percent are converted to acrylic acid, 1.5 percent to acetic acid, 1.1 percent to formaldehyde, 0.1 percent to maleic acid and 8.0 percent to waste gas.

EXAMPLE 10

A tungsten-iron catalyst having the formula $Sn_{.053}Sb_{0.05}Te_{0.36}As_{0.07}/Fe_{6.55}W_{12}P_{3.5}Sn_{1.62}Ni_{1.66}Mo_{0.28}Ox$ is prepared as follows:

To a 2 l. resin flask is charge 95 g. perlite, 123 g. phosphotungstic acid $(H_3(PW_{12}O_{40}).5.5H_2O)$, 103 g. ferric nitrate, 19 g. nickelous nitrate $(Ni(NO_3)_2.6H_2O)$, 22.4 g. stannic chloride $(SnCl_4.5H_2O)$, 565 ml. water and 40 ml. 70 percent nitric acid. 262 g. of a 14 percent ammonia solution is next added over a 40 minute period. Then, while applying vigorous agiation, the promoters are added. These consist of 2.2 g. tungsten telluride, 2.0 g. molybdenum telluride, 0.5 g. tin antimonide and 0.7 g. arsenic telluride, along with 26 g. perlite. While agitating vigorously, most of the water is stripped off and the resulting thick paste formed into 3/16 inch × 3/16 inch pellets. These are then calcined in air at 502° C. for 8 hours. These are tested for their utility in propylene oxidation, with the procedure being similar to that outlined earlier. At a 386° reactor temperature, 18 percent of the propylene is consumed. Conversions to the various products based on propylene fed, are: acrolein-9.2 percent, acrylic acid-0.1 percent, acetic acid-0.1 percent, acetaldehyde-0.0 percent and waste gas-7.5 percent.

EXAMPLE 11

The following comprises a comparison of the preferred, perlite supported, catalyst with unsupported iron-molybdate. This work is to demonstrate that the present invention is superior to iron molybdate, a catalyst of the prior art, which bears a superficial resemblance to the active ingredient of the present invention.

This material is prepared by stirring 1131 g. ferrous sulfate ($FeSO_4.7H_2O$) and 708 g. ammonium heptamolybdate, $(NH_4)_6Mo_7O_{24}.4H_2O$, in 2400 ml. deionized water at 65 to 70°. A solution, prepared by mixing 320 ml. deionized water and 320 ml. 29 percent ammonia, is then added dropwise over a 35 minute period. The olive green precipitate is filtered, washed 5 times with 5 2 l. portions of deionized water, and allowed to stand for 48 hours under 2 l. deionized water. The filter cake is dried and calcined in air at 608° to 643° for 8 hours. Oxidation tests are made with both propylene and isobutylene feedstocks, using methods outlined for the previous catalysts. In Tables II-A and II-B, data are presented for both the prior art composition and the present invention. The superiority of the latter is obvious. Synthesis of the "present invention catalyst" shown here is described in Example 7.

Table II-A

Comparison of the Preferred, Perlite Supported Catalyst with Unsupported Iron Molybdate Propylene Oxidation

| Catalyst | Reactor Temp. (° C.) | Conv. of $C_3H_6$ (%) | Percent Conversion to | | | |
|---|---|---|---|---|---|---|
| | | | Acrolein | AA[1] | HAc | Waste Gas |
| Present Invention | 422 | 22 | 16.6 | 1.5 | 0.2 | 3.4 |
| | 468 | 49 | 32.0 | 4.7 | 0.1 | 10.2 |
| Prior Art | 438 | 15 | 4.4 | 0.0 | 0.1 | 9.7 |
| | 470 | 14 | 0.0 | 0.0 | 0.0 | 16.1 |

[1] AA = acrylic acid

Table II-B

Comparison of the Preferred, Perlite Supported Catalyst with Unsupported Iron Molybdate Isobutylene Oxidation

| Catalyst | Reactor Temp. (° C.) | Conv. of $C_4H_8$ (%) | Percent Conversion of | | | |
|---|---|---|---|---|---|---|
| | | | MAcr | MAA | HAc | Waste Gas |
| Present Invention | 374.0 | 59. | 38.1 | 1.0 | 3.3 | 12.6 |
| Prior Art | 370.0 | 22. | 4.7 | 0.0 | 1.4 | 15.2 |

While the primary utility of the novel catalysts of the invention is in the preparation of methacrolein from isobutylene, other branched chain olefins may be oxidized and ammoxidation may be used to prepare such products as methacrylonitrile.

In all of the foregoing examples where perlite is used, before the catalyst is made the perlite has a total surface area of less than 15 m.$^2$/g., a total porosity of at least 2.5 cc./g., at least 40 percent of the pores being greater than 100,000 A in diameter, and no more than 25 percent of the pores being less than 10,000 A in diameter.

It is to be understood that in the foregoing wherever "hollow bubbles," "glassy bubbles," "microballoons," and "hollow spheres," are mentioned in connection with expanded perlite prior to its being crushed, applicants intend to include expanded particles having a foam-like structure wherein the tiny particles have a number of individual cells connected to one another. Such multicellular particles are illustrated in the article "Petrographic Techniques in Perlite Evaluation," Trans. AIME, Volume 226, pages 332-336, by F. L. Kadey, Jr. (1963).

We claim:

1. In a method of oxidizing isobutylene, at temperature of 350°-550° C in the vapor phase, the principal product, being methacrolein, the improvement of conducting said oxidation in the presence of a particulate calcined catalyst in the form of a metal oxide catalyst on a support consisting essentially of expanded perlite having, prior to formation and calcination of the catalyst, a total surface area of less than 15 m$^2$/g., a total porosity of at least 2.5 cc./g., at least 40 percent of the pores being greater than 100,000 A in diameter, and no more than 25 percent of the pores being less than 100,000 A in diameter.

2. The method of claim 1 in which said surface area is less than 10 m$^2$/g., the total porosity is at least about 2.8 cc./g., at least about 55 percent of the pores are greater than 100,000 A in diameter, and no more than about 15 percent of the pores are less than 10,000 A in diameter.

3. The method of claim 1 in which the total surface area is less than 5 m$^2$/g., the total porosity is greater than about 3 cc./g., at least about 60 percent of the pore volume exists as pores larger than 100,000 A, and no more than about 10 percent of the pore volume is present as pores of less than 10,000 A in size.

4. The method of claim 1 in which catalyst is based on an oxide combination selected from Co—Mo; Fe—Mo; Bi—Mo; Bi—Fe; Sb—U; —Fe, —Mn, —Th, —Ce, —Mo—, or —Sn; Mo—Zn or —Cd; Mo—Th; Mo—P; Cu—Te; Mo—Ca or —Mg; and combinations thereof.

5. The method of claim 2 in which the catalyst is based on an oxide combination selected from Co—Mo; Fe—Mo; Bi—Mo; Bi—Fe; Sb—U, —Fe, —Mn, —Th, —Ce, —Mo, or —Sn; Mo—Zn or —Cd; Mo—Th; Mo—P; Cu—Te; Mo—Ca or —Mg; and combinations thereof.

6. The method of claim 3 in which the catalyst is based on an oxide combination selected from Co—Mo; Fe—Mo; Bi—Mo; Bi—Fe; Sb—U, —Fe, —Mn, —Th, —Ce, —Mo, or —Sn; Mo—Zn or —Cd; Mo—Th; Mo—P; Cu—Te; Mo—Ca or —Mg; and combinations thereof.

7. The method of claim 4 in which the catalyst is based on Co—Mo, Fe—Mo, or mixtures thereof.

8. The method of claim 5 in which the catalyst is based on Co—Mo, Fe—Mo, or mixtures thereof.

9. The method of claim 6 in which the catalyst is based on Co—Mo, Fe—Mo, or mixtures thereof.

10. The method of claim 3 in which the catalyst is based on one having the empirical formula $Mo_{6-24}Co_{1-16}$, optionally with small amounts of activators or promoters, the perlite being smaller than 325 mesh.

11. The method of claim 3 in which the catalyst is based on one having the empirical formula $Mo_{12}Fe_{0.1-12}Bi_{0.1-12}$, optionally with small amounts of promoters or activators, the perlite being smaller than 325 mesh.

12. The method of claim 3 in which the catalyst is based on one having the empirical formula $Mo_{12}Bi_{0.1-12}$, optionally having small amounts of promotors or activators, the perlite being smaller than 325 mesh.

13. The method of claim 3 in which the catalyst is based on one having the empirical formula $Mo_{12}Fe_{2-12}$, optionally having small amounts of activators or promotors, the perlite being smaller than 325 mesh.

* * * * *